(12) United States Patent
Tran et al.

(10) Patent No.: US 6,656,950 B2
(45) Date of Patent: Dec. 2, 2003

(54) ANTIDEPRESSANT AZAHETEROCYCLYLMETHYL DERIVATIVES OF 1,4-DIOXINO[2,3-B] PYRIDINE

(75) Inventors: Megan Tran, Hoboken, NJ (US); Gary P. Stack, Ambler, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/127,923

(22) Filed: Apr. 23, 2002

(65) Prior Publication Data

US 2002/0183355 A1 Dec. 5, 2002

Related U.S. Application Data

(60) Provisional application No. 60/286,301, filed on Apr. 25, 2001.

(51) Int. Cl.⁷ .................. A61K 31/436; A61K 31/444; C07D 491/056; C07D 498/04; A61P 25/22; A61P 25/24
(52) U.S. Cl. .......... 514/302; 514/300; 514/321; 514/338; 546/115; 546/113; 546/197; 546/277.4
(58) Field of Search ................ 546/115, 113; 514/302, 300

(56) References Cited

U.S. PATENT DOCUMENTS

| | | |
|---|---|---|
| 5,468,767 A | 11/1995 | Cipollina et al. |
| 5,532,241 A | 7/1996 | Bottcher et al. |
| 5,741,789 A | 4/1998 | Hibschman et al. |
| 5,750,724 A | 5/1998 | Kang et al. |
| 5,869,490 A | 2/1999 | Stack |
| 5,977,106 A | 11/1999 | Patoiseau et al. |
| 6,559,169 B2 * | 5/2003 | Husbands ............ 514/338 |

FOREIGN PATENT DOCUMENTS

| | | |
|---|---|---|
| EP | 0 559 285 | 9/1993 |
| WO | WO 95/007274 | 3/1995 |
| WO | WO 96/24596 | 8/1996 |
| WO | WO 99/05140 | 2/1999 |
| WO | WO 01/14330 | 3/2001 |
| WO | WO 01/49680 | 7/2001 |

OTHER PUBLICATIONS

Alan M. Birch et al., J. Med. Chem., 1999, 3342–3355, 42.

* cited by examiner

*Primary Examiner*—Evelyn Mei Huang
(74) *Attorney, Agent, or Firm*—Woodcock Washburn LLP

(57) ABSTRACT

Compounds of the formula

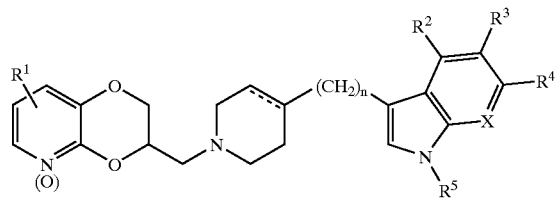

useful for the treatment of depression, obsessive compulsive disorder, panic attacks, generalized anxiety disorder, social anxiety disorder, sexual dysfunction, eating disorders, obesity, addictive disorders caused by ethanol or cocaine abuse, and dysthymia.

18 Claims, No Drawings

ANTIDEPRESSANT AZAHETEROCYCLYLMETHYL DERIVATIVES OF 1,4-DIOXINO[2,3-B] PYRIDINE

BACKGROUND OF THE INVENTION

This application claims priority from co-pending provisional application serial No. 60/286,301, filed on Apr. 25, 2001, the entire disclosure of which is hereby incorporated by reference.

Major depression is a serious health problem affecting more than 5% of the population, with a life-time prevalence of 15–20%.

Selective serotonin reuptake inhibitors have produced significant success in treating depression and related illnesses and have become among the most prescribed drugs. They nonetheless have a slow onset of action, often taking several weeks to produce their full therapeutic effect. Furthermore, they are effective in fewer than two-thirds of patients.

Serotonin selective reuptake inhibitors (SSRIs) are well known for the treatment of depression and other conditions. SSRIs work by blocking the neuronal reuptake of serotonin, thereby increasing the concentration of serotonin in the synaptic space, and thus increasing the activation of postsynaptic serotonin receptors.

However, although a single dose of an SSRI can inhibit the neuronal serotonin transporter which would be expected to increase synaptic serotonin, long-term treatment is required before clinical improvement is achieved.

It has been suggested that the SSRIs increase the serotonin levels in the vicinity of the serotonergic cell bodies and that the excess serotonin activates somatodendritic autoreceptors, $5HT_{1A}$ receptors, causing a decrease in serotonin release in major forebrain areas. This negative feedback limits the increment of synaptic serotonin that can be induced by antidepressants.

A $5HT_{1A}$ antagonist would limit the negative feedback and should improve the efficacy of the serotonin reuptake mechanism. (Perez, V., et al., *The Lancet*, 349:1594–1597 (1997)). Such a combination therapy would be expected to speed up the effect of the serotonin reuptake inhibitor.

Thus, it is highly desirable to provide improved compounds which both inhibit serotonin reuptake and which are antagonists of the $5HT_{1A}$ receptor.

DESCRIPTION OF THE INVENTION

In accordance with this invention, there is provided a group of novel compounds of the formula:

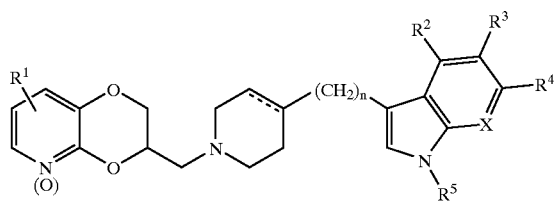

I wherein
$R^1$ is selected from hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$, $R^3$, $R^4$ and $R^6$ are independently selected from hydrogen, halo, cyano, trifluoromethyl, alkyl of 1 to 6 carbon atoms, alkoxy of 1 to 6 carbon atoms, and alkanoyloxy of 2 to 6 carbon atoms; and $R^5$ is hydrogen or alkyl of 1 to 6 carbon atoms;

X is $CR^6$ or N;

A dotted line represents an optional double bond;

(O) represents optional oxidation; and n is an integer 0, 1 or 2;

or a pharmaceutically acceptable salt thereof.

In some preferred embodiments of the present invention $R^1$ is hydrogen, hydroxy, halo, cyano, trifluoromethyl, amino, mono- or di-alkylamino in which each alkyl group has 1 to 6 carbon atoms, alkyl of one to six carbon atoms or alkoxy of one to six carbon atoms. In still more preferred embodiments $R^1$ is hydrogen.

In other preferred embodiments of the invention $R^2$, $R^3$ and $R^4$ are independently selected from hydrogen, halo, cyano, alkyl of one to six carbon atoms, or alkoxy of one to six carbon atoms. In still more preferred embodiments of the invention $R^2$, $R^3$ and $R^4$ are independently selected from hydrogen, cyano or halogen.

In still other preferred embodiments of the invention $R^3$ is hydrogen or lower alkyl.

X is preferably $CR^6$. When X is $CR^6$, then $R^6$ is preferably hydrogen, halo, cyano, alkyl of one to six carbon atoms or alkoxy of one to six carbon atoms, and more preferably hydrogen, cyano or halogen.

Of the compounds of Formula I, the preferred members are those in which $R^1$ is attached to the 6-position of the 1,4-dioxino[2,3-b]pyridine and is hydrogen, hydroxy, halo, cyano, trifluoromethyl, amino, mono- or di-alkylamino in which each alkyl group has 1 to 6 carbon atoms, alkyl of one to six carbon atoms or alkoxy of one to six carbon atoms; $R^2$, $R^3$ and $R^4$ are independently selected from hydrogen, halo, cyano, alkyl of one to six carbon atoms, or alkoxy of one to six carbon atoms; n is an integer 0 or 1; and $R^5$, X, (O) and the dotted line are defined as above.

Most preferred are those examples in which $R^1$ is hydrogen, hydroxy or alkoxy of one to six carbon atoms, $R^2$, $R^3$ and $R^4$ are independently selected from hydrogen, halo and cyano, $R^5$ is hydrogen, X is $CR^6$, $R^6$ is hydrogen, halo, or cyano, n is 0, (O) is defined as above and the dotted line represents a double bond.

This invention relates to both the R and S stereoisomers of the 3-amino-methyl-1,4-dioxino[2,3-b]pyridines, as well as to mixtures of the R and S stereoisomers. Throughout this application, the name of the product of this invention, where the absolute configuration of the 3-aminomethyl-1,4-dioxino[2,3-b]pyridines is not indicated, is intended to embrace the individual R and S enantiomers as well as mixtures of the two. In some embodiments of the present invention the S stereoisomer is preferred.

Where a stereoisomer is preferred, it may, in some embodiments be provided substantially free of the corresponding enantiomer. Thus, an enantiomer substantially free of the corresponding enantiomer refers to a compound which is isolated or separated via separation techniques or prepared free of the corresponding enantiomer. Substantially free as used herein means that the compound is made up of a significantly greater proportion of one stereoisomer. In preferred embodiments the compound is made up of at least about 90% by weight of a preferred stereoisomer. In other embodiments of the invention, the compound is made up of at least about 99% by weight of a preferred stereoisomer. Preferred stereoisomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

Furthermore, it is appreciated that, when $R^1$ is attached to the 6-position of the 1,4-dioxino[2,3-b]pyridine and is hydroxy, the molecule may exist as either the pyridone or pyridinol tautomer. The claims in this application or intended to embrace both tautomers, as well as mixtures of the two.

Alkyl as used herein refers to an aliphatic hydrocarbon chain and includes straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. Lower alkyl refers to alkyl having 1 to 3 carbon atoms.

Alkanamido as used herein refers to the group R—C(=O)—NH— where R is an alkyl group of 1 to 5 carbon atoms.

Alkanoyloxy as used herein refers to the group R—C(=O)—O— where R is an alkyl group of 1 to 5 carbon atoms.

Alkanesulfonamido as used herein refers to the group R—S(O)$_2$—NH— where R is an alkyl group of 1 to 6 carbon atoms.

Alkoxy as used herein refers to the group R—O— where R is an alkyl group of 1 to 6 carbon atoms.

Carboxamido as used herein refers to the group —CO—NH$_2$.

Carboalkoxy as used herein refers to the group R—O—C(=O)— where R is an alkyl group of 1 to 5 carbon atoms.

Halogen (or halo) as used herein refers to chlorine, bromine, fluorine and iodine.

Pharmaceutically acceptable salts are those derived from such organic and inorganic acids as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific compounds of the present invention include:

3-{[4-(1H-indol-3-yl)-3,6-dihydro-1(2H)-pyridinyl]methyl}-2,3-dihydro-[1,4]-dioxino[2,3-b]pyridine;

3-{[4-(5-fluoro-1H-indol-3-yl)-3,6-dihydro-1(2H)-pyridinyl]methyl}-2,3-dihydro-{1,4]dioxino[2,3-b]pyridine;

3-{1-[2,3-dihydro[1,4]dioxino[2,3-b]pyridin-3-ylmethyl]-1,2,3,6-tetrahydro-4-pyridinyl}-1H-indole-5-carbonitrile; and 3-{[4-(6-fluoro-1H-indol-3-yl)-3,6-dihydro-1(2H)-pyridinyl]methyl}-2,3-dihydro-[1,4]dioxino[2,3-b]pyridine; and pharmaceutical salts thereof.

The compounds of the invention are most conveniently prepared by the method outlined in Scheme I below. Unless otherwise noted, the variables are as defined above. Specifically, the appropriately substituted 2-bromo-3-pyridinol (1) is alkylated with glycidyl tosylate or nitrobenzenesulfonate or an epihalohydrin in the presence of a suitable base such as sodium hydride or potassium carbonate. The resulting glycidyl ether (2) is heated with the appropriate azaheterocycle in a high Scheme I

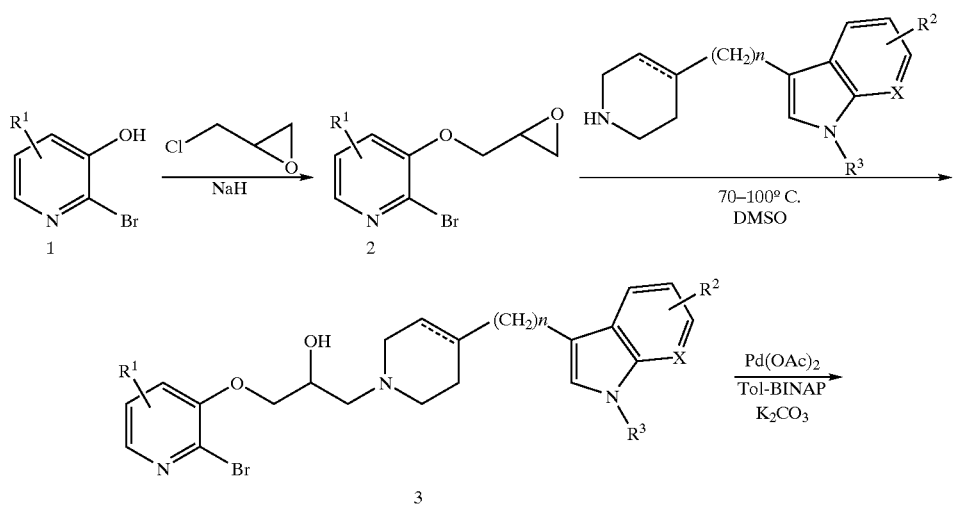

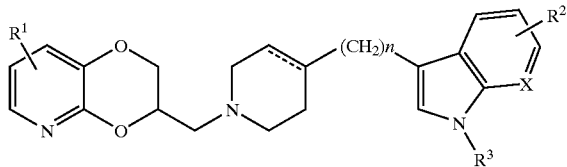

I boiling solvent such as dimethyl sulfoxide to effect an opening of the epoxide to a vicinal amino alcohol (3). Cyclization of the secondary alcohol to the title compounds of the invention is accomplished by treatment with catalytic palladium acetate and 2,2'-bis(di-p-tolylphosphino)-1,1'-binaphthyl [Tol-BINAP] in the presence of sodium or potassium carbonate.

suitable protecting group such as a t-butyl dimethylsilyl (TBS) ether to produce (5) and then cyclization to the pyridodioxan effected by treatment with catalytic palladium acetate and Tol-BINAP in the presence of potassium carbonate as described above to produce (6). Following deprotection of the pyridodioxan alcohol Scheme II

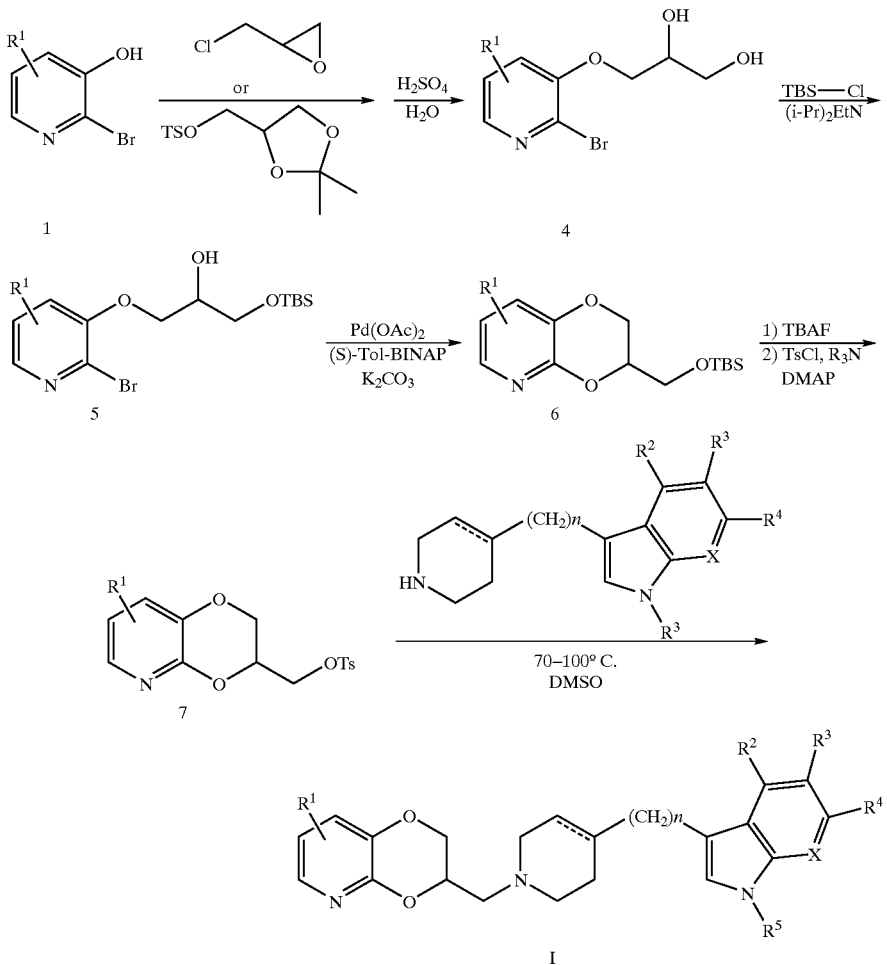

I

Alternatively, the appropriately substituted 2-bromo-3-pyridinol (1) may be alkylated either with an epihalohydrin or glycidyl tosylate as described above or with αβ-isopropylidene-γ-tosylate as shown in Scheme II below and then treated with dilute aqueous acid to give the vicinal diol (4). The primary alcohol is selectively protected with a via treatment with tetra-n-butylammonium fluoride (TBAF) in methanol and conversion to the tosylate with p-toluenesulfonyl chloride (TsCl) in the presence of a tertiary base and catalytic dimethylaminopyridine (DMAP) to produce (7), the title compounds of the invention are produced by reaction with the appropriate azaheterocycle in a high boiling solvent such as dimethylsulfoxide. Oxidation of the pyridodioxan-3-methyl tosylate or silyl ether with meta-chloroperoxybenzoic acid (m-CPBA) or hydrogen peroxide leads to the compounds of the invention which are pyridine-N-oxides.

The pyridine-N-oxide also allows convenient access to the compounds of the invention which are substituted in the 6-position as shown in Scheme III below. Treatment of the N-oxide (8) with phosphorus oxyhalide gives the 6-halo derivative (9), which can be treated with a primary or secondary amine to give the 6-mono- or dialkylamino derivatives (13), or with sodium cyanide to give the 6-nitrile. Treatment of the N-oxide with acetic anhydride, followed by hydrolysis with mild base, gives the 6-hydroxy derivative (11). Treatment of the N-oxide with p-toluenesulfonyl chloride followed by the appropriate alcohol gives the 6-alkoxy derivative (12). Treatment of the N-oxide with trimethysilyl azide and reduction with hydrogen over palladium on carbon yields the 6-amino derivative (10). Replacement of the tosylate with the appropriately substituted azaheterocycle as described above gives the title compounds of the invention.

sion and other diseases commonly treated by the administration of serotonin selective reuptake inhibitor (SSRI) antidepressants, such as obsessive compulsive disorder, panic attacks, generalized anxiety disorder, social anxiety disorder, sexual dysfunction, eating disorders, obesity, addictive disorders caused by ethanol or cocaine abuse and related illnesses. Moreover, the compounds of this invention have potent affinity for and antagonist activity at brain 5-HT$_{1A}$ serotonin receptors. Recent clinical trials employing drug mixtures (eg, fluoxetine and pindolol) have demonstrated a more rapid onset of antidepressant efficacy for a treatment combining SSRI activity and 5-HT$_{1A}$ antagonism (Blier and Bergeron, 1995; F. Artigas et. al., 1996; M. B. Tome et. al., 1997). The compounds of the invention are thus exceedingly interesting and useful for treating depressive illnesses.

A protocol similar to that used by Cheetham et. al. (Neuropharmacol. 32:737, 1993) was used to determine the affinity of the compounds of the invention for the serotonin transporter. The compound's ability to displace $^3$H-paroxetine from male rat frontal cortical membranes was

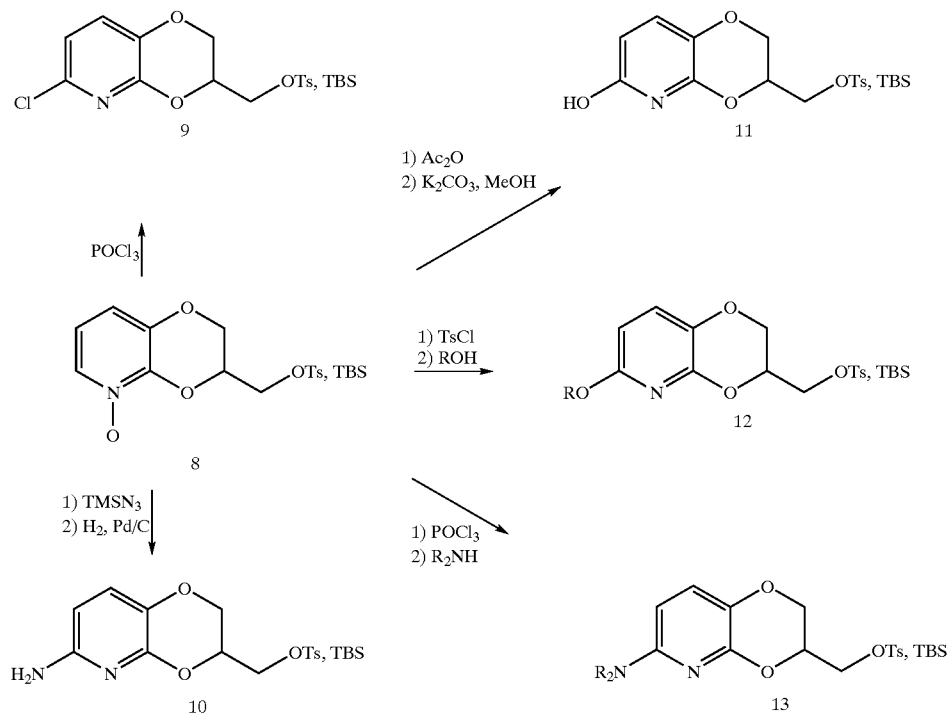

Scheme III

The azaheterocycles appropriate to the invention are known compounds or they can be prepared by one schooled in the art. The compounds of the invention may be resolved into their enantiomers by conventional methods or, preferably, they may be prepared directly by substitution of (2R)-(−)-glycidyl tosylate or (R)-α, β-isopropylidene-γ-tosylate (for the R pyridodioxan-3-methylamine) or (2S)-(+)-glycidyl tosylate or (S)-α, β-isopropylidene-γ-tosylate (for the S enantiomer) in place of epichlorohydrin in the procedures above.

Like the antidepressants fluoxetine, paroxetine and sertraline, the compounds of this invention have the ability to potently block the reuptake of the brain neurotransmitter serotonin. They are thus useful for the treatment of depresdetermined using a Tom Tech filtration device to separate bound from free $^3$H-paroxetine and a Wallac 1205 Beta Plate® counter to quantitate bound radioactivity. $K_i$'s thus determined for standard clinical antidepressants are 1.96 nM for fluoxetine, 14.2 nM for imipramine and 67.6 nM for zimelidine. A strong correlation has been found between $^3$H-paroxetine binding in rat frontal cortex and $^3$H-serotonin uptake inhibition.

High affinity for the serotonin 5-HT$_{1A}$ receptor was established by testing the claimed compound's ability to displace [$^3$H] 8-OHDPAT (dipropylaminotetralin) from the 5-HT$_{1A}$ serotonin receptor following a modification of the procedure of Hall et al., J. Neurochem. 44, 1685 (1985) which utilizes CHO cells stably transfected with human 5-HT$_{1A}$ receptors.

The 5-HT$_{1A}$ affinities for the compounds of the invention are reported below as K$_i$'s.

Antagonist activity at 5-HT$_{1A}$ receptors was established by using a $^{35}$S-GTPγS binding assay similar to that used by Lazareno and Birdsall (Br. J. Pharmacol. 109: 1120, 1993), in which the test compound's ability to affect the binding of $^{35}$S-GTPγS to membranes containing cloned human 5-HT$_{1A}$ receptors was determined. Agonists produce an increase in binding whereas antagonists produce no increase but rather reverse the effects of the standard agonist 8-OHDPAT. The test compound's maximum inhibitory effect is represented as the I$_{max}$, while its potency is defined by the IC$_{50}$.

The results of the three standard experimental test procedures described in the preceding three paragraphs were as follows:

| Compound | 5-HT Transporter Affinity KI (nM) | 5-HT$_{1A}$ Receptor Affinity KI (nM) | 5-HT$_{1A}$ Function IC$_{50}$ (nM) (I$_{max}$) |
|---|---|---|---|
| Example 1 | 9.50 | 14.30 | 197.0 (62.0) |
| Example 2 | 2.39 | 6.81 | 57.0 (94.0) |
| Example 3 | 2.58 | 22.40 | 183 (100%) |
| Example 4 | 1.21 | 10.16 | 618.0 (77.0) |

Hence, the compounds of this invention are combined serotonin reuptake inhibitors/5-HT$_{1A}$ antagonists and are useful for the treatment of diseases commonly treated by the administration of serotonin selective reuptake inhibitor (SSRI) anti-depressants, such as depression (including but not limited to major depressive disorder, childhood depression and dysthymia), anxiety, panic disorder, post-traumatic stress disorder, premenstrual dysphoric disorder (also known as pre-menstrual syndrome), attention deficit disorder (with and without hyperactivity), obsessive compulsive disorder (including trichotillomania), social anxiety disorder, generalized anxiety disorder, obesity, eating disorders such as anorexia nervosa, bulimia nervosa, vasomotor flushing, cocaine and alcohol addiction, sexual dysfunction (including premature ejaculation), and related illnesses.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in *Remingtons Pharmaceutical Sciences*, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of the present invention are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age and response pattern of the patient. Generally, a starting dose is about 5 mg per day with gradual increase in the daily dose to about 150 mg per day, to provide the desired dosage level in the human.

Provide as used herein means either directly administering a compound or composition of the present invention, or administering a prodrug, derivative or analog which will form an equivalent amount of the active compound or substance within the body.

The present invention includes prodrugs of compounds of Formula I. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985);

Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991), Bundgaard, et al., Journal of Drug Deliver Reviews, 8:1–38(1992), Bundgaard, J. of Pharmaceutical Sciences, 77:285 et seq. (1988); and Higuchi and Stella (eds.) Prodrugs as Novel Drug Delivery Systems, American Chemical Society (1975).

The following examples illustrate the production of representative compounds of this invention.

Intermediate 1

2-Bromo-3-[oxiranylmethoxy]pyridine

To a mixture of 25.2 g (0.145 mole) of 2-bromo-3-pyridinol and 30 g (0.22 mole) of potassium carbonate in 80 mL of N,N-dimethylformamide was added 30 g (0.13 mole) of (S)-glycidyl tosylate. The mixture was heated under nitrogen at 55–60° C. for 15 hours. The solvent was then removed in vacuum and replaced with 500 mL of methylene chloride, and the solution was washed with 500 mL of water and with saturated brine, dried over sodium sulfate, filtered and concentrated in vacuum. The residue was column chromatographed on silica gel with methylene chloride as eluant to give 17 g of the (S)-enantiomer of the title compound as a white solid. $^1$H-NMR (CDCl$_3$): multiplet 8.01 δ (1 H); multiplet 7.22 δ (2 H); doublet of doublets 4.38 δ (1 H); multiplet 4.04 δ (1 H); multiplet 3.40 δ (1 H); multiplet 2.95 δ (1 H); multiplet 2.85 δ (1 H).

EXAMPLE 1

3-{[4-(1H-Indol-3-yl)-3,6-dihydro-1(2H)-pyridinyl]methyl}-2,3-dihydro[,1,4]dioxino[2,3-b]pyridine 3-(1,2,3,6-Tetrahydro-4-pyridinyl)-1H-indole (1.03 g, 5.22 mmole) and 2-bromo-3-[(2S)-oxiranylmethoxy]pyridine (0.80 g, 3.47 mmole) were combined in DMSO (25 mL). This solution was heated at 75–80° C. under nitrogen for 5 hours. After completion, the reaction was cooled to room temperature and partitioned between 250 mL each of ethyl acetate and saturated sodium bicarbonate. The organic phase was washed with brine, dried over magnesium sulfate and concentrated in vacuum. The crude residue was column chromatographed on silica gel using first methylene chloride as eluant to remove impurities and then 3% methanol in methylene chloride to elute the product, which upon concentration in vacuum, gave a yellow solid (1.05 g, 71%). 0.55 g (1.28 mmole) of this yellow intermediate was then cyclized in toluene (50 mL) in the presence of palladium (II) acetate (0.015 g, 0.061 mmole), (S)-(−)-2,2'-bis(di-p-tolylphosphino)-1,1'-binaphthyl (0.052 g, 0.077 mmole), and potassium carbonate (0.21 g, 1.5 mmol). The heterogeneous mixture was heated to 100° C. for a period of 24 hours. After the mixture cooled to room temperature, the catalysts were removed by filtration and the filtrate was concentrated to a crude brown oil, which was then column chromatographed on silica gel with 3% methanol in methylene chloride as eluant to give the desired product as a brown oil (0.23 g, 52%). The oil was crystallized from ethanol with the addition of a solution of oxalic acid (0.04 g) in hot ethanol to give 0.10 g of the (S)-enantiomer of the title compound as a yellow solid oxalate, m.p. 116° C.

Elemental Analysis for: $C_{21}H_{21}N_3O_2.C_2H_2O_4.H_2O$
Calc'd: C, 60.65; H, 5.53; N, 9.23
Found: C, 60.94; H, 5.32; N, 8.89

EXAMPLE 2

3-{[4-(5-Fluoro-1H-indol-3-yl)-3,6-dihydro-1(2H)-pyridinyl]methyl}-2,3-dihydro{1,4]dioxino[2,3-b]pyridine 5-Fluoro-3-(1,2,3,6-tetrahydro-4-pyridinyl)-1H-indole (1.16 g, 5.37 mmole) and 2-bromo-3-[(2S)-oxiranylmethoxy]pyridine (0.83 g, 3.6 mmole) were combined in DMSO (40 mL). This solution was heated at 75–80° C. under nitrogen for 5 hours. After completion, the reaction was cooled to room temperature and partitioned between 250 mL each of ethyl acetate and saturated sodium bicarbonate. The organic phase was washed with brine, dried over magnesium sulfate and concentrated in vacuum. The crude residue was column chromatographed on silica gel using first methylene chloride as eluant to remove impurities and then 3% MeOH/CH$_2$Cl$_2$ to elute the product, which was a yellow solid (0.90 g, 56%). The intermediate (0.90 g, 2.01 mmole) was then cyclized in toluene (40 mL) in the presence of palladium (II) acetate (0.02 g, 0.09 mmole), (S)-(−)-2,2'-bis(di-p-tolylphosphino)-1,1'-binaphthyl (0.085 g, 0.12 mmole), and potassium carbonate (0.33 g, 2.4 mmole). The heterogeneous mixture was heated to 100° C. for a period of 24 hours. After the mixture cooled to room temperature, the catalysts were removed by filtration and the filtrate was concentrated in vacuum. The resulting crude brown oil was then column chromatographed on silica gel with 3% methanol in methylene chloride to give the desired product as a brown oil (0.23 g, 33%). The oil was crystallized from ethanol with the addition of a solution of oxalic acid (0.05 g) in hot ethanol to give 0.24 g of the (S)-enantiomer of the title compound as a white solid hemioxalate, m.p. 124° C.

Elemental Analysis for: $C_{21}H_{20}FN_3O_2.0.50 C_2H_2O_4.H_2O$
Calc'd: C, 61.68; H, 5.41; N, 9.80
Found: C, 61.96; H, 5.02; N, 9.80

EXAMPLE 3

3-{1-[2,3-Dihydro[1,4]dioxino[2,3-b]pyridin-3-ylmethyl]-1,2,3.6-tetrahydro-4-pyridinyl}-1H-indole-5-carbonitrile 3-(1,2,3,6-Tetrahydro-4-pyridinyl)-1H-indole-5-carbonitrile (1.62 g, 7.26 mmole) and 2-bromo-3-[(2S)-oxiranylmethoxy]pyridine (0.84 g, 3.65 mmol) were combined in DMSO (40 mL). This solution was heated at 75–80° C. under nitrogen for 5 hours. After completion, the reaction was cooled to room temperature and partitioned between 250 mL each of ethyl acetate and saturated sodium bicarbonate. The organic phase was washed with brine, dried over magnesium sulfate and concentrated in vacuum. The crude residue was column chromatographed on silica gel using first methylene chloride as eluant to remove impurities and then 3% methanol in methylene chloride to elute the product, which was a yellow foam (0.30 g, 18%). The intermediate (0.30 g, 0.66 mmole) was then cyclized in toluene (40 mL) in the presence of palladium (II) acetate (0.015 g, 0.067 mmole), (S)-(−)-2,2'-Bis(di-p-tolylphosphino)-1,1'-binaphthyl (0.032 g, 0.047 mmole), and potassium carbonate (0.13 g, 0.94 mmole). The heterogeneous mixture was heated at 100° C. for a period of 30 hours. After the mixture cooled to room temperature, the catalysts were removed by filtration and the filtrate was concentrated in vacuum. The resulting crude brown oil was then column chromatographed on silica gel with 3% methanol in methylene chloride to give the desired product as a brown oil (0.100 g, 42%). The oil was crystallized from ethanol with the addition of a solution of oxalic acid in hot ethanol to give 0.050 g of the (S)-enantiomer of the title compound as a white solid, m.p. 165° C.

Elemental Analysis for: $C_{22}H_{20}N_4O_2.1.4C_2H_2O_4$
Calc'd: C, 59.76; H, 5.61; N, 11.24
Found: C, 59.77; H, 4.95; N, 10.89

EXAMPLE 4

3-{4-(6-Fluoro-1H-indol-3-yl)-3,6-dihydro-1(2H)-pyridinyl]methyl}-2,3-dihydro[1,4]dioxino[2,3-b]pyridine 6-Fluoro-3-(1,2,3,6-tetrahydro-4-pyridinyl)-1H-indole (1.87 g, 8.65 mmole) and 2-bromo-3-[(2S)- oxiranylmethoxy]pyridine (1.00 g, 4.34 mmole) were combined in DMSO (45 mL). This solution was heated at 75–80° C. under nitrogen for 5 hours. After completion, the reaction was cooled to room temperature and partitioned between 250 mL each of ethyl acetate and saturated sodium bicarbonate. The organic phase was washed with brine, dried over magnesium sulfate and concentrated in vacuum. The crude oil was column chromatographed on silica gel using first methylene chloride as eluant to remove impurities and then 3% methanol in methylene chloride to elute the product, which was a yellow solid (0.30 g, 15%). The intermediate (0.30 g, 0.67 mmole) was then cyclized in toluene (40 mL) in the presence of palladium (II) acetate (0.010 g, 0.044 mmole), (S)-(–)-2,2'-bis(di-p-tolylphosphino)-1,1'-binaphthyl (0.030 g, 0.044 mmole), and potassium carbonate (0.11 g, 0.80 mmole). The heterogeneous mixture was heated at 100° C. for a period of 24 hours. After the mixture cooled to room temperature, the catalysts were removed by filtration and the filtrate was concentrated in vacuum. The resulting crude brown oil was then column chromatographed on silica gel with 3% methanol in methylene chloride to give the desired product as a brown oil (0.19 g, 79%). The oil was crystallized from ethanol with the addition of a solution of oxalic acid in hot ethanol to give 0.070 g of the (S)-enantiomer of the title compound as beige solid dioxalate, m.p. 120° C.

Elemental Analysis for: $C_{21}H_{20}FN_3O_2 \cdot 2C_2H_2O_4$
Calc'd: C, 55.05; H, 4.43; N, 7.70
Found: C, 55.40; H, 4.42; N, 7.48

What is claimed is:

1. A compound of formula I

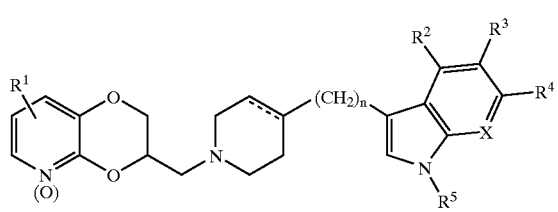

I wherein
$R^1$ is selected from hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;
$R^2$, $R^3$, $R^4$ and $R^6$ are independently selected from hydrogen, halo, cyano, trifluoromethyl, alkyl of 1 to 6 carbon atoms, alkoxy of 1 to 6 carbon atoms, and alkanoyloxy of 2 to 6 carbon atoms; and
$R^5$ is hydrogen or alkyl of 1 to 6 carbon atoms;
X is $CR^6$ or N;
A dotted line represents an optional double bond;
(O) represents optional oxidation; and
n is an integer 0, 1 or 2;
or a pharmaceutically acceptable salt thereof.

2. A compound of claim 1 wherein $R^1$ is hydrogen.

3. A compound of claim 1 wherein $R^2$, $R^3$ and $R^4$ are independently selected from hydrogen, halogen, and cyano.

4. A compound of claim 1 wherein $R^5$ is hydrogen or lower alkyl.

5. A compound of claim 1 wherein X is $CR^6$.

6. A compound of claim 5 wherein $R^6$ is hydrogen, halogen or cyano.

7. A compound of claim 1 in which $R^1$ is attached to the 6-position of the 1,4-dioxino[2,3-b]pyridine and is hydrogen, hydroxy, halo, cyano, trifluoromethyl, amino, mono- or di-alkylamino in which each alkyl group has 1 to 6 carbon atoms, alkyl of one to six carbon atoms or alkoxy of one to six carbon atoms; $R^2$, $R^3$ and $R^4$ are independently selected from hydrogen, halo, cyano, alkyl of one to six carbon atoms, and alkoxy of one to six carbon atoms; n is an integer 0 or 1; or a pharmaceutically acceptable salt thereof.

8. A compound of claim 1 in which $R^1$ is attached to the 6-position of the 1,4-dioxino[2,3-b]pyridine and is hydrogen, hydroxy or alkoxy of one to six carbon atoms, $R^2$, $R^3$ and $R^4$ are independently selected from hydrogen, halo and cyano, $R^5$ is hydrogen, X is $CR^6$, n is 0, and the dotted line represents a double bond; or a pharmaceutically acceptable salt thereof.

9. A compound of claim 7 wherein $R^6$ is hydrogen, halo or cyano.

10. The compound of claim 1 which 3-{[4-(1H-indol-3-yl)-3,6-dihydro-1(2H)-pyridinyl]methyl}-2,3-dihydro[1,4]dioxino[2,3-b]pyridine or a pharmaceutically acceptable salt thereof.

11. The compound of claim 1 which is 3-{[4-(5-fluoro-1H-indol-3-yl)-3,6-dihydro-1(2H)-pyridinyl]methyl}-2,3-dihydro{1,4]dioxino[2,3-b]pyridine or a pharmaceutically acceptable salt thereof.

12. The compound of claim 1 which is 3-{1-[2,3-dihydro[1,4]dioxino[2,3-b]pyridin-3-ylmethyl]-1,2,3,6-tetrahydro-4-pyridinyl}-1H-indole-5-carbonitrile or a pharmaceutically acceptable salt thereof.

13. The compound of claim 1 which is 3-{[4-(6-fluoro-1H-indol-3-yl)-3,6-dihydro-1(2H)-pyridinyl]methyl}-2,3-dihydro[1,4]dioxino[2,3-b]pyridine or a pharmaceutically acceptable salt thereof.

14. A method of treating a subject suffering from a condition selected from depression, anxiety, panic disorder, post-traumatic stress disorder, premenstrual dysphoric disorder, attention deficit disorder, obsessive compulsive disorder, social anxiety disorder, and generalized anxiety disorder, which comprises providing to the subject suffering from said condition, a therapeutically effective amount of a compound of formula I

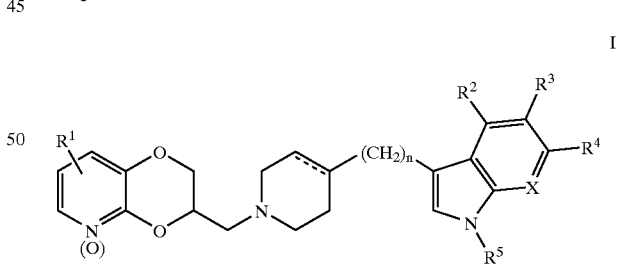

I wherein
$R^1$ is selected from hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;
$R^2$, $R^3$, $R^4$ and $R^6$ are independently selected from hydrogen, halo, cyano, trifluoromethyl, alkyl of 1 to carbon atoms, alkoxy of 1 to 6 carbon atoms, and alkanoyloxy of 2 to 6 carbon atoms; and $R^5$ is hydrogen or alkyl of 1 to 6 carbon atoms;

X is $CR^6$ or N;

A dotted line represents an optional double bond;

(O) represents optional oxidation; and n is an integer 0, 1 or 2;

or a pharmaceutically acceptable salt thereof.

15. The method of claim 13 wherein wherein the condition is depression.

16. The method of claim 13 wherein the condition is obsessive compulsive disorder, panic attacks, generalized anxiety disorder or social anxiety disorder.

17. The method of claim 13 wherein the subject is a human.

18. A pharmaceutical composition comprising a compound of formula I

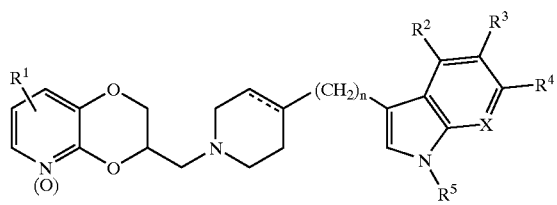

wherein $R^1$ is selected from hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$, $R^3$, $R^4$ and $R^6$ are independently selected from hydrogen, halo, cyano, trifluoromethyl, alkyl of 1 to 6 carbon atoms, alkoxy of 1 to 6 carbon atoms, and alkanoyloxy of 2 to 6 carbon atoms; and $R^5$ is hydrogen or alkyl of 1 to 6 carbon atoms;

X is $CR^6$ or N;

A dotted line represents an optional double bond;

(O) represents optional oxidation; and n is an integer 0, 1 or 2;

or a pharmaceutically acceptable salt thereof, and a pharmaceutically acceptable carrier or excipient.

* * * * *